US010017465B2

(12) United States Patent
Schäfer et al.

(10) Patent No.: US 10,017,465 B2
(45) Date of Patent: Jul. 10, 2018

(54) METHOD FOR PRODUCING ASTAXANTHIN FROM ASTACIN

(71) Applicant: BASF SE, Ludwigshafen (DE)

(72) Inventors: Bernd Schäfer, Dierbach (DE); Wolfgang Siegel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/502,827

(22) PCT Filed: Jul. 23, 2015

(86) PCT No.: PCT/EP2015/066902
§ 371 (c)(1),
(2) Date: Feb. 9, 2017

(87) PCT Pub. No.: WO2016/023732
PCT Pub. Date: Feb. 18, 2016

(65) Prior Publication Data
US 2017/0233338 A1    Aug. 17, 2017

(30) Foreign Application Priority Data

Aug. 12, 2014  (EP) .................................... 14180726

(51) Int. Cl.
*C07C 403/24*  (2006.01)
*B01J 31/02*  (2006.01)
*B01J 31/22*  (2006.01)

(52) U.S. Cl.
CPC ......... *C07C 403/24* (2013.01); *B01J 31/0222* (2013.01); *B01J 31/2291* (2013.01); *B01J 31/2295* (2013.01); *B01J 2231/645* (2013.01); *B01J 2531/821* (2013.01); *C07B 2200/07* (2013.01); *C07C 2601/16* (2017.05)

(58) Field of Classification Search
CPC .......................... C07C 403/24; C07C 2601/16
USPC ....................................................... 568/343
See application file for complete search history.

(56) References Cited

U.S. PATENT DOCUMENTS

| | | | |
|---|---|---|---|
| 4,283,559 A | 8/1981 | Broger et al. | |
| 5,625,099 A | 4/1997 | Ernst et al. | |
| 6,590,111 B2 | 7/2003 | Grimmer et al. | |
| 6,699,911 B2 | 3/2004 | Grimmer et al. | |
| 2006/0088905 A1 | 4/2006 | Lockwood et al. | |

FOREIGN PATENT DOCUMENTS

| | | |
|---|---|---|
| DE | 10049271 A1 | 4/2002 |
| EP | 0005748 A2 | 12/1979 |
| EP | 0633258 A1 | 1/1995 |
| EP | 1285912 A2 | 2/2003 |

OTHER PUBLICATIONS

Francis, G., et al., "Animal Carotenoids: 6. The Structures of Roserythrin and the Parent Nor-Carotenoid", Acta Chemica Scandinavica, vol. 26, No. 3, (1972), pp. 1097-1104.
Hall, E., et al., "Electrochemical Reductive Acylation of Astacene; a Route to the Cartenoid Astaxanthin", Journal of the Chemical Society, Chemical Communications, No. 9, (1978), pp. 387-388.
International Search Report for PCT/EP2015/066902 dated Oct. 1, 2015.
International Search Report for PCT/EP2015/067674 dated Oct. 15, 2015.
Widmer, E., et al., "Technische Verfahren zur Synthese von Carotinoiden und verwandten Verbindungen aus 6-Oxo-isophoron. V. Syntese von Astacin", Helvetica Chimica Acta, vol. 65, No. 3, (1982), pp. 671-683.
Written Opinion of the International Searching Authority for PCT/EP2015/066902 dated Oct. 1, 2015.
Written Opinion of the International Searching Authority for PCT/EP2015/067674 dated Oct. 15, 2015.
Zell, R., et al., "Technische Verfahren zur Synthese von Carotinoiden und verwandten Verbindungen aus 6-Oxo-isophoron. III. Ein neues Konzept für die Synthese der enantiomeren Astaxanthine", Helvetica Chimica Acta, vol. 64, No. 7, (1981), pp. 2447-2462.

*Primary Examiner* — Sikarl A Witherspoon
(74) *Attorney, Agent, or Firm* — Drinker Biddle & Reath LLP

(57) ABSTRACT

The invention relates to a method for the non-stereoselective and also for the stereoselective synthesis of astaxanthin from astacin. For this purpose, a reducing agent is used selected from the group of hydrogen, a secondary alcohol, formic acid and also the salts of formic acid or from a mixture of at least two representatives of the compound classes stated above. The invention further relates to the use of astacin as starting compound for the synthesis of astaxanthin.

19 Claims, No Drawings

METHOD FOR PRODUCING ASTAXANTHIN FROM ASTACIN

CROSS-REFERENCE TO RELATED APPLICATIONS

This application is a national stage application (under 35 U.S.C. § 371) of PCT/EP2015/066902, filed Jul. 23, 2015, which claims benefit of European Application No. 14180726.3, filed Aug. 12, 2014, both of which are incorporated herein by reference in their entirety.

The present invention relates to a method for preparing astaxanthin from astacin. The present invention further comprises the use of astacin for preparing astaxanthin in various isomeric forms.

Industrial syntheses of astaxanthin have been described in detail both in the relevant literature, e.g. G. Britton, S. Liaaen-Jensen, H. Pfander, Carotenoids, Vol. 2, Birkhäuser Verlag, Basle, 1996, 283 ff., and in various textbooks, e.g. B. Schafer, Naturstoffe der chemischen Industrie (Natural Substances of the Chemical Industry), Akademischer Verlag, Heidelberg, 2007, 427 ff., in scientific journals, e.g. K. Meyer, Chemie in unserer Zeit (Chemistry in Our Time) 36 (2002) 178 and also in the patent literature, e.g. DE 10049271 A1 or EP 1285912 A2.

Although of considerable industrial interest, the selective hydrogenation of the double bonds in position Δ 2,3 or Δ 2',3' of astacin for preparing astaxanthin is completely unknown to date. The following statement is found only in E. Widmer, T. Lukác, K. Bernhard, R. Zell, Helv. Chim. Acta 65 (1982) 671:

"Astacin is of particular interest as potential starting material for the synthesis of astaxanthin. However, no method for the regioselective hydrogenation of the 2,3-double bonds is known to date. An electrochemical reduction under acylating conditions has already been achieved, however, which allowed the isolation of astaxanthin in a yield of 10%" [E. A. H. Hall, G. P. Moss, J. H. P. Utley, B. C. L. Weedon, Chem. Commun. (1978) 387].

However, yields of 10%, based on the amount of astacin used, are not satisfactory on an industrial scale. In addition, the astaxanthin from the electrolytic method mentioned above is obtained as a mixture of astaxanthin, astacin and 2,3-didehydroastaxanthin. Such complex mixtures can only be separated into their individual constituents with difficulty. Pure or highly enriched stereoisomers of astanxanthin are obtained to an even lesser degree with this method.

However, it is not only the electrochemical synthesis of astaxanthin from astacin that is less than satisfactory. The preparation of this molecule under Ramberg-Backlund conditions also does not afford high yields of astaxanthin, but rather large amounts of astacin which to date cannot be economically further processed to astaxanthin. Thus, Choi & Koo, J. Org. Chem. 70 (2005) on p. 3330, right column, in the latter third of the second paragraph reads: "The base-promoted dehydrosulfonation reaction of 11c using NaOEt in refluxing EtOH/benzene gave rise to astacene (3) in 71% yield instead of astaxanthin (2). Apparently, the silicon protecting groups were desilylated in the course of the harsh dehydrosulfonation reaction, and the resulting astaxanthin (2) was readily oxidized to astacene (3) in the presence of base and traces of oxygen.[25]"

Widmer comes to the result in Helv. Chim. Acta. 65(3) 1982 671ff on p. 678 in the last paragraph combined with p. 679 Scheme 10, that the chemistry of carotenoids having a $C_{40}$ base structure is difficult. It states: "It was thus once more demonstrated that chemical reactions on carotenoids already built up to the $C_{40}$ stage may often be linked to major problems, especially as the purification of the resulting mixtures is difficult".

Against this background, an object to be achieved for the person skilled in the art consists in overcoming the problems of the prior art and in finding a method to convert astacin selectively to astaxanthin. Selectively means that functional groups present, other than the two enol groups in the astacin—or the corresponding keto groups of the tautomeric form—do not react or only react to a very low extent. In particular, a method should be provided which regioselectively reduces the double bonds in position $\Delta^{2,3}$ or $\Delta^{2',3'}$ of astacin to give astaxanthin. By-products or the reactant astacin itself should be barely formed or only in small amounts. The method should be feasible with simple apparatus and on an industrial scale. It should also be inexpensive and simple to perform, i.e. to proceed without many intermediates or complex method steps and workup steps.

A further object consists of reacting astacin stereoselectively, that is to say, reacting such that to a large degree and as far as possible only one stereoisomer of astanxanthin is formed as target compound in each case. In particular, a method should be provided which stereoselectively reduces the double bonds in position $\Delta^{2,3}$ or $\Delta^{2',3'}$ of astacin to give astaxanthin. The stereoselective reaction should also be simple to perform and applicable on an industrial scale. The reaction should also comprise as few method steps and workup steps as possible and be cost-effective.

A final object consists of finding a novel precursor as starting material for the synthesis of astaxanthin, in which the asymmetric center in position 3,3' of the astaxanthin is optionally racemic or has (S) or (R) configuration.

The main features of the achievement of these objects of the invention are obtained from claims 1 and 15. Configurations are the subject matter of claims 2 to 14.

The objects mentioned above are achieved by a method for preparing astaxanthin of the formula 1,

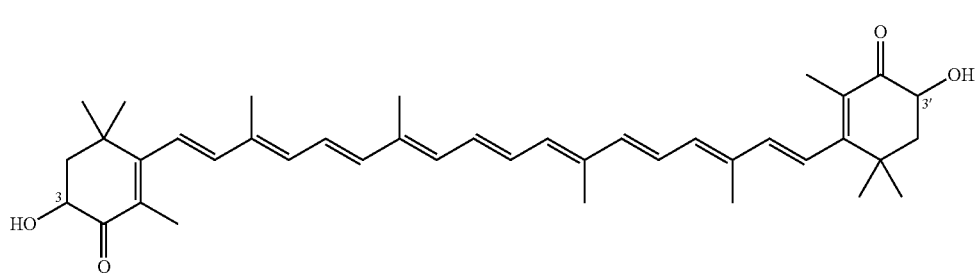

1 in which the asymmetric center in position 3 and 3' is racemic or each has (S) or (R) configuration and the exocyclic double bonds have either E or E and/or Z configuration. This method according to the invention is characterized in that the astacin of the formula 2,

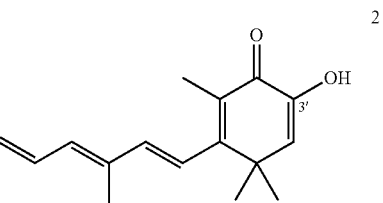

in which the exocyclic double bonds have either E or E and/or Z configuration, is reacted non-stereoselectively or stereoselectively with a reducing agent.

Such a result could not have been predicted since, in addition to the enolized carbonyl in position 3 and/or 3', the person skilled in the art would assume that at least one of the other functional groups of the compound 2, i.e. the carbonyl in position 4 or 4' and/or at least one of the exocyclic double bonds, would likewise be reduced. A person skilled in the art would expect that the tetraol below is formed with nickel catalysts and the compound of type A with palladium catalysts.

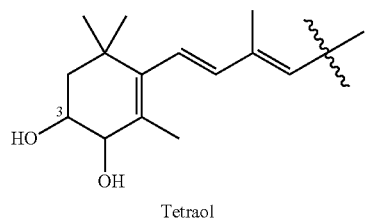

Tetraol

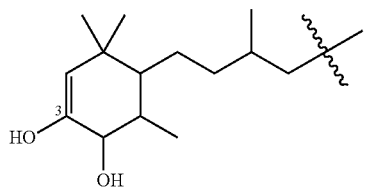

A

"Non-stereoselectively" means that the reaction of the reactant due to the reducing agent leads to a product with no steric preference.

"stereoselectively" is understood to mean that the reducing agent gives rise to products, namely enantiomers or diastereomers, in which predominantly only one configuration, as far as possible exclusively one configuration, is formed at the site of reduction (at the stereocenter).

The astacin 2 used as starting compound according to the invention may also be regarded as the tautomeric diketone according to the equilibrium shown below.

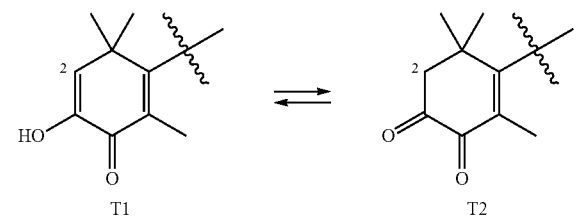

In the context of this invention, therefore, the term "astacin" includes not only the tautomer T1 but in each case always the tautomer T2 as well.

In addition, the term "astacin of the formula 2" or "astacin 2" does not only comprise the all-trans isomer, as shown in the structure above, but also any Z isomer which derives from the all-trans isomer and also mixtures of at least two of these isomers. "Z isomer" signifies that at least one of the exocyclic double bonds of the astacin 2 is present in the Z conformation.

The term "astaxanthin of the formula 1" or "astaxanthin 1" is understood to mean, in addition to the all-trans isomer, as shown in the structure above, also any Z isomer which derives from the all-trans isomer and also mixtures of at least two of these isomers. "Z isomer" signifies that at least one of the exocyclic double bonds of the astaxanthin 1 is present in the Z conformation.

The astaxanthin of the formula 1 is as defined in the latter paragraph with respect to its stereo-chemistry at position 3,3' and is apportionable to "astaxanthin of the formula 1a"

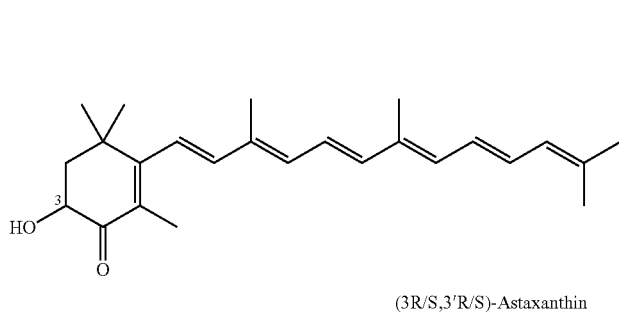
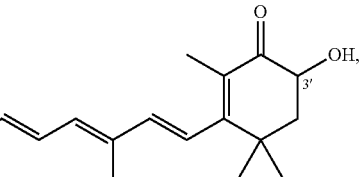

(3R/S,3′R/S)-Astaxanthin which is understood to mean any racemic mixture with respect to the positions 3,3' or else the meso form;

to "astaxanthin of the formula 1b"

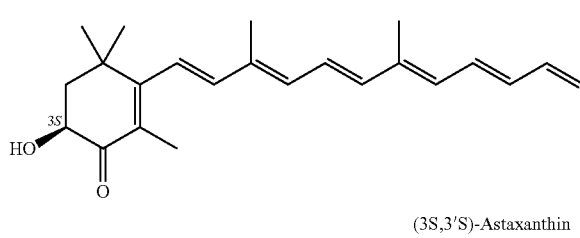
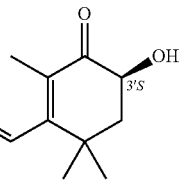

(3S,3′S)-Astaxanthin and to "astaxanthin of the formula 1c"

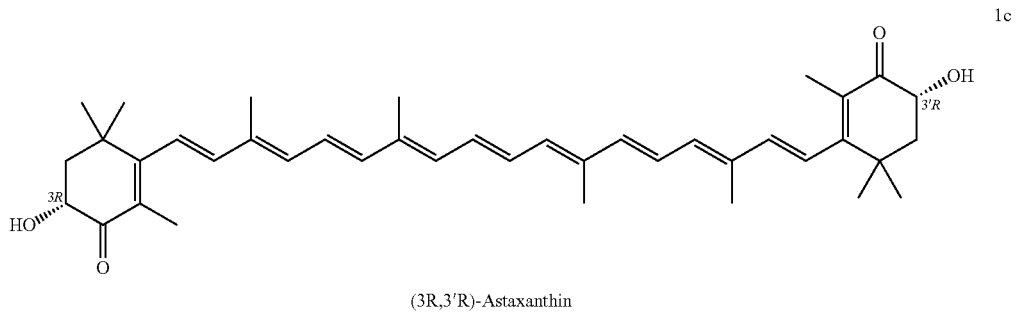 [SMILES: CC1=C(/C=C/C(C)=C/C=C/C(C)=C/C=C/C=C(C)/C=C/C=C(C)/C=C/C2=C(C)C(=O)[C@H](O)CC2(C)C)C(C)(C)C[C@@H](O)C1=O]

(3R,3′R)-Astaxanthin

The formulae 1a, 1b and 1c of astaxanthin also comprise in each case the all-trans isomers, any Z isomers and also mixtures of at least two of these isomers, as explained above for the terms "astaxanthin of the formula 1" or "astaxanthin 1".

The term reducing agent comprises all those compounds which are suitable to convert astacin 2 to astaxanthin 1. In a preferred continuation, the term reducing agent is understood to mean all those compounds which convert astacin 2 into astaxanthin 1, without reacting with other functional groups of the astacin 2.

A continuation of the invention provides that the reducing agent is at least one compound selected from the group consisting of hydrogen gas; a secondary alcohol, preferably isopropanol or butan-2-ol; formic acid, the salts of formic acid, particularly an alkali metal, alkaline earth metal or ammonium formate or a mono-, di-, tri- or tetra(C1-C4)-alkylammonium formate.

A secondary alcohol is a compound in which two alkyl groups are located on the carbon atom in the ipso position, wherein alkyl includes any group with the overall formula $C_nH_{2n+1}$. Secondary alcohols are selected from the group consisting of propan-2-ol, butan-2-ol, 3-methylbutan-2-ol, 3,3-dimethylbutan-2-ol, pentan-2-ol, pentan-3-ol, 2-methylpentan-3-ol, 3-methylpentan-2-ol, 4-methylpentan-2-ol, 2,2-dimethylpentan-3-ol, 2,4-dimethylpentan-3-ol, 3,3-dimethylpentan-2-ol, 4,4-dimethylpentan-2-ol, 2,2,4-trimethylpentan-3-ol, 2,2,4,4-tetramethylpentan-3-ol, hexan-2-ol, hexan-3-ol, 2-methylhexan-3-ol, 3-methylhexan-2-ol, 4-methylhexan-2-ol, 4-methylhexan-3-ol, 4-ethylhexan-3-ol, 5-methylhexan-2-ol, 5-methylhexan-3-ol, 2,2-dimethylhexan-3-ol, 2,4-dimethylhexan-3-ol, 2,5-dimethylhexan-3-ol, 4-isopropyl-2-methylhexan-3-ol, 2,2,5,5-tetramethylhexan-3-ol, heptan-2-ol, heptan-3-ol, 2-methylheptan-3-ol, 2-methylheptan-4-ol, 3-methylheptan-2-ol, 4-methylheptan-2-ol, 4-methylheptan-3-ol, 5-methylheptan-2-ol, 5-methylheptan-3-ol, 6-methylheptan-2-ol, 2,2-dimethylheptan-3-ol, 2,6-dimethylheptan-3-ol, 2,6-dimethylheptan-4-ol, 3,5-dimethylheptan-4-ol, 3,6-dimethylheptan-2-ol, 2,5,6-trimethylheptan-4-ol, octan-2-ol, octan-3-ol, octan-4-ol, 2-methyloctan-4-ol, 2-methyloctan-5-ol, 3-methyloctan-2-ol, 3-methyloctan-4-ol, 2,2-dimethyloctan-3-ol, 2,4-dimethyloctan-3-ol, 2,6-dimethyloctan-3-ol, 3,7-dimethyloctan-2-ol, nonan-2-ol, nonan-4-ol, nonan-5-ol, nonan-3-ol, 2-methylnonan-4-ol, 2-methylnonan-3-ol, 3-methylnonan-2-ol, 5-methylnonan-4-ol, 5-ethylnonan-2-ol, 5-butylnonan-2-ol, 2,2-dimethylnonan-3-ol, 2,6,8-trimethylnonan-4-ol, decan-2-ol, decan-3-ol, decan-4-ol, decan-5-ol, 2-methyldecan-3-ol, 5-methyldecan-4-ol, undecan-2-ol, undecan-3-ol, undecan-5-ol, undecan-6-ol, 2-methylundecan-3-ol, 5-methylundecan-6-ol, 6-methylundecan-5-ol, 6-pentylundecan-5-ol, 7-ethyl-2-methylundecan-4-ol, dodecan-2-ol, dodecan-3-ol, dodecan-5-ol, dodecan-4-ol, dodecan-6-ol, 2-methyldodecan-3-ol, 3,7,11-trimethyldodecan-4-ol, tridecan-2-ol, tridecan-3-ol, tridecan-4-ol, tridecan-7-ol, 2-methyltridecan-3-ol, tetradecan-2-ol, tetradecan-3-ol, tetradecan-4-ol, tetradecan-6-ol, 2-methyltetradecan-3-ol, 3,7-dimethylpentadecan-2-ol, 6,10,14-trimethylpentadecan-2-ol, hexadecan-2-ol, hexadecan-6-ol, 9-octylheptadecan-10-ol, dicapryl alcohol.

Among these secondary alcohols, preference is given to the alcohols isopropanol and/or butan-2-ol, since they are inexpensive and also on reduction form acetone or methyl ethyl ketone, two solvents which can be readily removed due to their low boiling points. In addition, they ensure partial solubility of the compounds 1 and 2.

In a further configuration, the reducing agent is preferably at least one compound selected from the group of formic acid and/or salts of formic acid. These compounds are inexpensive to acquire. Moreover, carbon dioxide is released on reduction thereof, which can be released continuously from the reaction vessel without much difficulty or released at the end of the reaction. In relation to the apparatus, a simple and targeted reaction procedure is possible. In addition, the workup of the reaction mixture is considerably simplified and thus the costs of the preparation process are reduced.

Salts of formic acid are all those compounds comprising a formate anion and an organic or inorganic cation as counterion.

A mono-, di-, tri- or tetra(C1-C4)-alkylammonium formate comprises a formate anion and a nitrogen-bearing cation as counterion. The nitrogen-bearing cation is an ammonium ion, which comprises four hydrogen atoms in addition to nitrogen or has one (mono), two (di), three (tri) or four (tetra) alkyl groups instead of hydrogen. The at least one alkyl group is a C1-C4-alkyl group, i.e. it is selected from methyl, ethyl, n-propyl, isopropyl, n-butyl, sec-butyl, isobutyl, tert-butyl.

Particularly suitable and inexpensive formic acid salts for the method according to the invention comprise trimethylammonium formate, triethylammonium formate, tri-n-butylammonium formate, ethyldiisopropylammonium formate, tetrabutylammonium formate or a mixture of at least two of these salts.

The reducing agent is particularly preferably an alkali metal salt or an alkaline earth metal salt or an ammonium salt of formic acid or a mixture of at least two of these compounds. In addition to the gaseous carbon dioxide, by-products occur in the reduction with one of these reducing agents which are either present dissolved in a polar phase or are precipitated in the form of a salt. Removal from the reaction product is thereby particularly simple.

In a particularly preferred developed embodiment, the reducing agent is at least one compound selected from the group consisting of sodium formate, potassium formate, magnesium formate, calcium formate and from the ammonium salts, from ammonia, i.e. ammonium formate. These reducing agents have in common that they are very inexpensive, since the formates of sodium, potassium, magnesium and calcium, and also those of ammonia are readily accessible and are available from various suppliers. Ammonium formate also has the advantage that ammonia is liberated at elevated temperature. It can be seen that excess ammonium formate can be decomposed and removed at the end of the reduction by heating.

In a further variant, the reducing agent is selected from the group of the formates of primary amines, in particular from the formate of at least one of the amines methylamine, ethylamine, n-propylamine, isopropylamine, n-butylamine, sec-butylamine, tert-butylamine, isobutylamine, n-pentylamine, aniline, benzylamine.

In another configuration of the invention, the reducing agent is at least one compound selected from the group consisting of secondary or tertiary amines of formic acid. Secondary amines of formic acid are formed from a formate ion as anion and a simple protonated N,N-dialkylamine as cation.

Secondary amines of formic acid comprise the formate of dimethylamine, of diethylamine, of di-n-propylamine, of di-n-butylamine or a mixture of at least two of these compounds.

Tertiary amines of formic acid consist of a formate ion as anion and a simple protonated N,N,N-trialkylamine as cation.

Tertiary amines of formic acid comprise the formate of trimethylamine, of triethylamine, of tri-n-propylamine, of tri-n-butylamine, of ethyldiisopropylamine or a mixture of at least two of these compounds.

In yet another modification of the invention, the reducing agent is at least one compound selected from the group of quaternary ammonium salts of formic acid. Quartenary ammonium salts of formic acid are compounds consisting of a formate ion as anion and an N,N,N,N-tetraalkylammonium ion as cation.

Quaternary salts of formic acid comprise, for example, tetraethylammonium formate, tetrabutylammonium formate, triisopropylethylammonium formate.

In a further configuration, the reducing agent is preferably at least one compound selected from the group of the salts of formic acid, in which the salts are generated in situ by neutralization of formic acid with an appropriate base. This base is selected from the group of ammonia and/or primary amines and/or secondary amines and/or tertiary amines. Such salts generated from formic acid are then always particularly of advantage if the salt is only to be formed slowly or if salt compounds which are not readily commercially available are to be used.

In a further configuration, the reducing agent is preferably at least one compound selected from the group of the salts of formic acid, in which the salts are used as such. Such salts have proven to always be favorable if they are obtainable inexpensively and can be easily stored and a reaction-dependent minimum or maximum concentration of these salts does not have to be regulated by in situformation.

The method according to the invention is further pursued in that the astacin 2 is reacted non-stereoselectively or stereoselectively with the reducing agent in the presence of a transition metal catalyst; preferably in the presence of an achiral or optically active transition metal catalyst. This means that the further object formulated above was achieved in a further inventive version by a transition metal-catalyzed hydrogenation, wherein the catalysts used are optionally achiral, enantiomerically enriched or enantiomerically pure transition metal catalysts. These catalysts significantly accelerate the reduction according to the invention and thus contribute to cost reduction.

A transition metal catalyst is understood to mean a compound which accelerates a reaction. Said catalyst comprises at least one transition metal, i.e. at least one metal of the third to twelfth group of the periodic table and at least one ligand.

An optically active transition metal catalyst is likewise a compound which accelerates a reaction. Said catalyst comprises at least one transition metal of the third to twelfth group of the periodic table and at least one optically active ligand.

Optically active ligands are those ligands which are capable of rotating, to a greater or lesser extent, the plane of polarization of a beam of linearly polarized light.

It has been shown that the transition metal catalyst having a transition metal selected from the group consisting of Ti, Zr, Hf, V, Nb, Ta, Cr, Mo, W, Mn, Re, Fe, Ru, Os, Co, Rh, Ir, Ni, Pd, Pt, Cu, Ag and Au could be used for the method according to the invention. The transition metals Zr, Nb, Mo, W, Ru, Co, Rh, Ir, Ni, Pd are particularly suitable by reason of their relative availability and/or their reactivity, particularly the transition metals Mo, Ru, Co, Rh, Ir, Ni, Pd. Particularly good results were obtained with the transition metals Ru, Ir, Ni, Pd in appropriate ligand arrangement. Finally, in the experiments conducted, ruthenium (Ru) has proven to be particularly suitable for the method according to the invention, since high yields of astaxanthin 1 were obtainable, without noticeable reaction, as far as possible no reaction at all, of the carbonyl group at position 4 and other functional groups of the astacin 2.

The transition metal catalyst preferably comprises a transition metal atom and at least one optionally achiral or optically active ligand, which is suitable for the reduction of the double bond at position $\Delta^{2,3}$ (equivalent to a keto group in position 3) of the astacin 2, to give the corresponding secondary alcohol. In principle, it is possible to use all transition metals which can form a suitable transition metal catalyst as transition metal atoms, such as Ti, Zr, Hf, V, Nb, Ta, Cr, Mo, W, Mn, Re, Fe, Ru, Os, Co, Rh, ir, Ni, Pd, Pt, Cu, Ag or Au.

A further provision of the inventive method is that the transition metal catalyst comprises at least one ligand selected from amines and/or phosphanes. In particular, the ligand is selected from amines and/or phosphanes and/or aromatic compounds and/or halides. In this case, the aromatic compounds are bonded to the transition metal complex and optionally covalently bonded to an amine or phosphane ligand. Such species have proven to be particularly suitable as far as coordination with a transition metal is concerned.

In particular, it has been found that the astacin 2 is then reacted non-stereoselectively or stereoselectively particularly with the reducing agent in the presence of a transition metal catalyst; preferably in the presence of an optically active transition metal catalyst, when the transition metal of the transition metal catalyst is ruthenium (Ru) and the ligand is selected from amines.

The phosphane ligand is preferably a phosphane of the general formula 3,

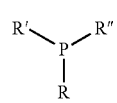

3 where R, R' and R" are each independently selected from the group consisting of one of the residues C1-C4-alkyl, phenyl, mono- up to tri-C1-C4-alkyl-substituted aryl; preferably a triarylphosphane and especially preferably triphenylphosphane.

C1-C4-alkyl is a group selected from methyl, ethyl, n-propyl, isopropyl, n-butyl, sec-butyl, isobutyl, tert-butyl. Aryl comprises all aromatic base structures, particularly phenyl and benzyl. C1-C4-alkyl-substituted aryl is an aryl, as previously defined, which is linked to one, two, three, four or five C1-C4-alkyl residues, as previously defined.

The following configuration of the method according to the invention affords protection of an outstanding aspect. Said configuration claims that the transition metal catalyst comprises at least one ligand selected from the group consisting of $H_2N$—$CH_2$—$CH_2$—OH, MeHN—$CH_2$—$CH_2$—OH, $H_2N$—$CH_2$—$CH_2$—$NH_2$, TsNH—$CH_2$—$CH_2$—$NH_2$, TsNH—$CH_2$—$CH_2$—NH—$(CH_2)_n$—$O_m$—$(CH_2)_o$-aryl where n=1-4, m=0 or 1 and o=1-4 and aryl=phenyl or mono-, di-, tri-C1-C4-alkylphenyl, optically active compound. With this type of ligand, racemic astaxanthin 1a was obtainable in yields of 631%, as shown in example 2.

A particular development of the invention thus provides a method for preparing astaxanthin of the formula 1

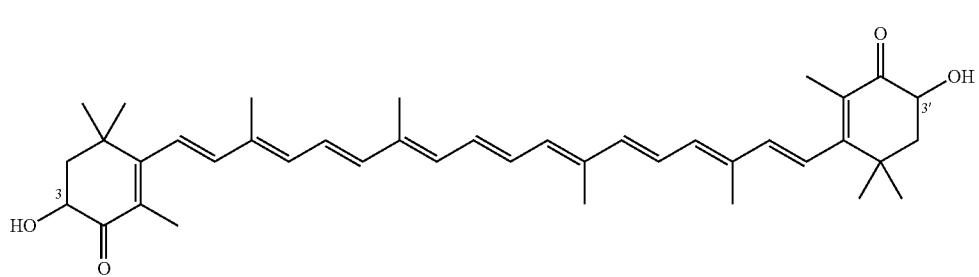

1 in which the asymmetric center in position 3 and 3' is racemic or has (S) or (R) configuration and the exocyclic double bonds have either E or E and/or Z configuration, wherein astacin of the formula 2,

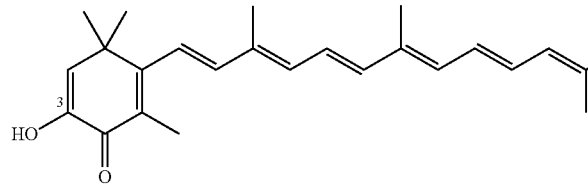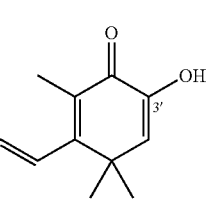

in which the exocyclic double bonds have either E or E and/or Z configuration, is reacted non-stereoselectively or stereoselectively with a reducing agent selected from the group consisting of formic acid and/or the salts of formic acid, isopropanol, butan-2-ol, in the presence of a transition metal catalyst, wherein the transition metal catalyst comprises ruthenium (Ru) as transition metal and at least one ligand selected from the group consisting of $H_2N$—$CH_2$—$CH_2$—OH, MeHN—$CH_2$—$CH_2$—OH, $H_2N$—$CH_2$—$CH_2$—$NH_2$, TsNH—$CH_2$—$CH_2$—$NH_2$, TsNH—$CH_2$—$CH_2$—NH—$(CH_2)_n$—$O_m$—$(CH_2)_o$-aryl where n=1-4, m=0 or 1 and o=1-4 and aryl=phenyl or mono-, di-, tri-C1-C4-alkylphenyl, optically active compound.

According to this method according to the invention, which describes a non-stereoselective reduction and in the case of the optically active compound either a non-stereoselective or a stereoselective reduction, racemic mixtures of astaxanthin 1 are produced which are sufficient for many applications.

The transition metal catalysts required for the racemic mixtures can be generated, for example, by reacting a suitable ruthenium compound, such as, for example $[RuX_2(\eta^6-Ar)]_2$, with a suitable ligand, where X is a halogen atom such as fluorine, chlorine, bromine or iodine, and Ar is benzene or a substituted benzene derivative, in particular a benzene derivative substituted with C1-C4-alkyl residues. C1-C4-alkyl is as already defined above.

However, in addition to optically inactive astaxanthin, there is also a need for optically active astaxanthin.

In the method according to the invention, therefore, an optically active transition metal catalyst is particularly preferably used which comprises a transition metal atom and at least one optically active ligand, wherein the transition metal atom is ruthenium (Ru). This means that the astacin 2 is reacted stereoselectively with the reducing agent in the presence of an optically active transition metal catalyst, wherein the transition metal catalyst comprises a transition metal atom and at least one optically active ligand and the transition metal atom is ruthenium (Ru).

Preferred chiral, particularly optically active ruthenium catalysts can be generated, for example, by reacting a suitable ruthenium compound, such as, for example $[RuX_2(\eta^6-Ar)]_2$, with a suitable chiral, particularly optically active ligand, where X is a halogen atom such as fluorine, chlorine, bromine or iodine, and Ar is benzene or a substituted benzene derivative, in particular a benzene derivative substituted with C1-C4-alkyl residues. C1-C4-alkyl is as already defined above. The chiral, particularly optically active ruthenium catalyst is preferably characterized in that the optically active ligand is an optically active amine or an optically active amino acid. Examples of optically active amines, which may be reacted with a suitable ruthenium compound, in particular $[RuX_2(\eta^6-Ar)]_2$, to give the catalytically active complex, are $H_2N$—CHPh-CHPh-OH, $H_2N$—CHMe-CHPh-OH, MeHN—CHMe-CHPh-OH, TsNH—CHPh-CHPh-$NH_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide or N-[(1R,2R)-1,2-diphenyl-2-(2-(4-methylbenzyloxy)ethylamino)ethyl]-4-methylbenzene sulfonamide, particularly (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide or N-[(1R,2R)-1,2-diphenyl-2-(2-(4-methylbenzyloxy)ethylamino)ethyl]-4-methylbenzene sulfonamide.

Therefore, a further important configuration of the invention provides that the transition metal catalyst comprises at least one ligand selected from the group consisting of an optically active amine, in particular $H_2N$—CHPh-CHPh-OH, $H_2N$—CHMe-CHPh-OH, MeHN—CHMe-CHPh-OH, TsNH—CHPh-CHPh-$NH_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide, N-[(1R,2R)-1,2-diphenyl-2-(2-(4-methylbenzyloxy)ethylamino)ethyl]-4-methylbenzene sulfonamide, an optically active amino acid; and is preferably selected from the group consisting of $H_2N$—CHPh-CHPh-OH, $H_2N$—CHMe-CHPh-OH, MeHN—CHMe-CHPh-OH, TsNH—CHPh-CHPh-$NH_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide, N-[(1R,2R)-1,2-diphenyl-2-(2-(4-methylbenzyloxy)ethylamino)ethyl]-4-methylbenzene sulfonamide. The preferred ligands are characterized in that they particularly readily form a complex with the transition metal. This transition metal complex is very stable under the conditions of the method according to the invention.

The transition metal catalyst according to the invention comprises the ligands mentioned in the latter paragraph, and is used as a simple and efficient route to prepare highly stereoisomerically enriched, or even stereoisomerically pure, astaxanthin 1 in good yields from astacin 2, as shown below.

For this reason, this is also a particularly important development essential to the invention. This development comprises a method for preparing astaxanthin of the formula 1

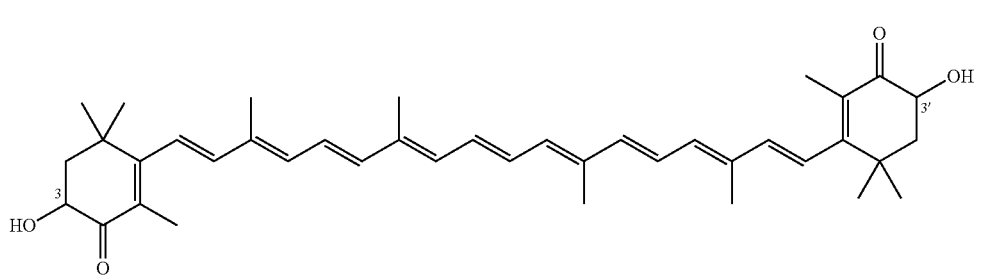

in which the asymmetric center in position 3 and 3' has (S) or (R) configuration and the exocyclic double bonds have either E or E and/or Z configuration, in which astacin of the formula 2 according to the invention,

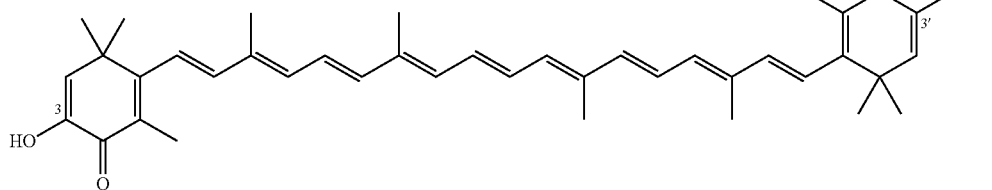

in which the exocyclic double bonds have either E or E and/or Z configuration, is reacted stereoselectively with a reducing agent selected from the group consisting of formic acid, the salts of formic acid, isopropanol or butan-2-ol, in the presence of an optically active, preferably an enantiomerically pure, transition metal catalyst, wherein the optically active, preferably the enantiomerically pure transition metal catalyst comprises ruthenium (Ru) as transition metal and at least one ligand selected from the group consisting of $H_2N$—CHPh-CHPh-OH, $H_2N$—CHMe-CHPh-OH, MeHN—CHMe-CHPh-OH, TsNH—CHPh-CHPh-$NH_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide, N-[(1R,2R)-1,2-diphenyl-2-(2-(4-methylbenzyloxy)ethylamino)ethyl]-4-methylbenzene sulfonamide, an optically active amino acid.

The other stereoisomers in each case, i.e. the other enantiomer or the diastereomer of the astaxanthin 1, only occur in very low amounts in this method and preferably not at all.

For example, if (1S,2S)—N-p-toluenesulfonyl-1,2-diphenylethylenediamine is used as optically active ligand in the method according to the invention, the compound of the formula (3S,3'S-1b) is obtained in high enantiomeric purity, while the use of (1R,2R)—N-p-toluenesulfonyl-1,2-diphenylethylenediamine as optically active ligand generates the compound of the formula (3R,3'R-1c).

In the method according to the invention, it has been found that most of the transition metal catalysts, including most of the chiral transition metal catalysts, are particularly efficient if at least one ligand thereof is mono-deprotonated.

Particular preference is also given to a chiral ruthenium catalyst, in which the optically active ligand is obtainable by mono-deprotonation of $H_2N$—CHPh-CHPh-OH, $H_2N$—CHMe-CHPh-OH, MeHN—CHMe-CHPh-OH or TsNH—CHPh-CHPh-$NH_2$, in particular by mono-deprotonation of (1S,2S)—N-p-toluenesulfonyl-1,2-diphenylethylenediamine or (1R,2R)—N-p-toluenesulfonyl-1,2-diphenylethylenediamine.

Thus, a configuration of the method according to the invention provides that the ligand selected, particularly the ligand selected from amines, is deprotonated, preferably mono-deprotonated.

In a modified embodiment, the method according to the invention provides that the transition metal catalyst comprises at least one ligand selected from the group consisting of $H_2N$—$CH_2$—$CH_2$—OH, MeHN—$CH_2$—$CH_2$—OH, $H_2N$—$CH_2$—$CH_2$—$NH_2$, TsNH—$CH_2$—$CH_2$—$NH_2$, TsNH—$CH_2$—$CH_2$—NH—$(CH_2)_n$—$O_m$—$(CH_2)_o$-aryl where n=1-4, m=0 or 1 and o=1-4 and aryl=phenyl or mono-, di-, tri-C1-C4-alkylphenyl, optically active chiral unit, wherein this ligand is linked to an aromatic compound optionally via a linker.

A further configuration of the method according to the invention specifies that the transition metal catalyst comprises at least one ligand selected from the group consisting of an optically active amine, in particular $H_2N$—CHPh-CHPh-OH, $H_2N$—CHMe-CHPh-OH, MeHN—CHMe-CHPh-OH, TsNH—CHPh-CHPh-$NH_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide, N-[(1R,2R)-1,2-diphenyl-2-(2-(4-methylbenzyloxy)ethylamino)ethyl]-4-methylbenzene sulfonamide, an optically active amino acid; and is preferably selected from the group consisting of $H_2N$—CHPh-CHPh-OH, $H_2N$—CHMe-CHPh-OH, MeHN—CHMe-CHPh-OH, TsNH—CHPh-CHPh-$NH_2$, (1S,2S)—N-p-toluenesulfonyl-1,2-diphenylethylenediamine, (1R,2R)—N-p-toluenesulfonyl-1,2-diphenylethylenediamine, N-[(1S, 2S)-1,2-diphenyl-2-(2-(4-methylbenzyloxy)ethylamino) ethyl]-4-methylbenzene sulfonamide, N-[(1R,2R)-1,2-diphenyl-2-(2-(4-methylbenzyloxy)ethylamino)ethyl]-4-methylbenzene sulfonamide, wherein this ligand is linked to an aromatic compound optionally via a linker.

To remove transition metal catalysts from a reaction mixture an additional filtration or extraction step is required. This step is essential for many of these transition metal catalysts since they would partially or totally lose their catalytic activity in any fixing or immobilizing process. Some transition metal catalysts are not, however, affected by such fixing. Thus, a very economically designed variant of the method according to the invention provides that the transition tions, preferably in a pH range of 8 to 12, wherein the bases used for this purpose are selected from the group consisting of ammonia, trimethylamine, triethylamine, tri-n-propylamine, tri-n-butylamine, diisopropylethylamine or a mixture of at least two of these compounds.

In particular, said embodiment signifies the provision of a method for preparing astaxanthin of the formula 1

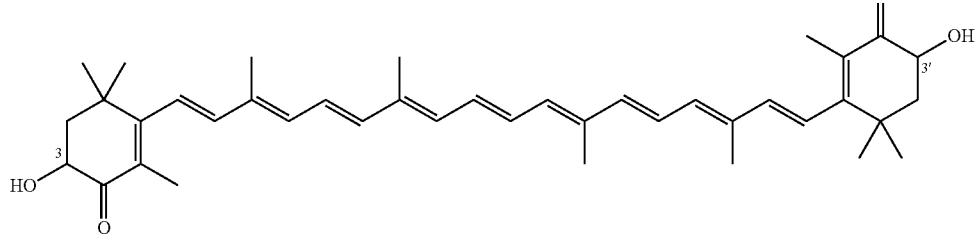

in which the asymmetric center in position 3 and 3' is racemic or has (S) or (R) configuration and the exocyclic double bonds have either E or E and/or Z configuration, in which astacin of the formula 2 according to the invention,

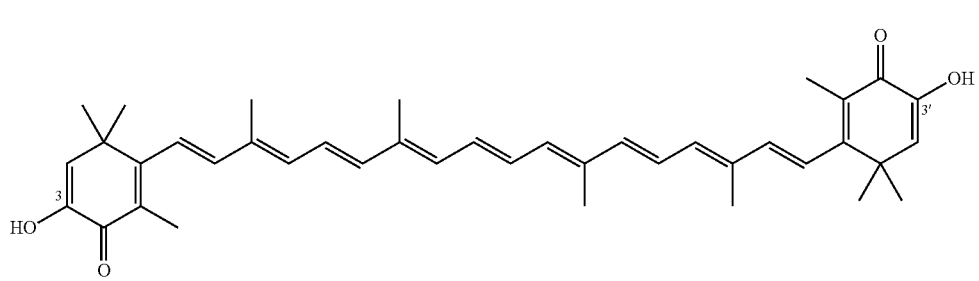

metal is applied to a solid support; preferably to a solid support comprising at least one substance selected from the group consisting of carbon, aluminum oxide and silicon dioxide; and most preferably to a solid support constructed from at least one substance selected from the group consisting of carbon, aluminum oxide and silicon dioxide.

According to this embodiment, a separation of the transition metal catalyst from the reaction product astaxanthin 1, in the sense of a separate method step, is avoided.

The reduction of astacin 2 was investigated at very different pH values with the result that a complete, or virtually complete, reaction to the corresponding astaxanthin 1 is possible only in a basic medium.

A further aspect of the invention, therefore, provides that astacin 2 is reacted non-stereoselectively or stereoselectively with a reducing agent under basic conditions, preferably in a pH range of 8 to 12.

Either the amine ligands already given above serve as bases and/or additional base is added.

The base used, particularly as additional base, is ammonia, trimethylamine, triethylamine, tri-n-propylamine, tri-n-butylamine, diisopropylethylamine or a mixture of at least two of these compounds.

Therefore, a further refined embodiment of the invention specifies that astacin 2 is reacted non-stereoselectively or stereoselectively with a reducing agent under basic conditions in which the exocyclic double bonds have either E or E and/or Z configuration, is reacted non-stereoselectively or stereoselectively under basic conditions, preferably in a pH range of 8 to 12, with a reducing agent selected from the group consisting of formic acid and/or the salts of formic acid, isopropanol, butan-2-ol, in the presence of a transition metal catalyst, wherein the transition metal catalyst comprises ruthenium (Ru) as transition metal and at least one ligand selected from the group consisting of $H_2N$—$CH_2$—$CH_2$—OH, MeHN—$CH_2$—$CH_2$—OH, $H_2N$—$CH_2$—$CH_2$—$NH_2$, TsNH—$CH_2$—$CH_2$—$NH_2$, TsNH—$CH_2$—$CH_2$—NH—$(CH_2)_n$—$O_m$—$(CH_2)_o$-aryl where n=1-4, m=0 or 1 and o=1-4 and aryl=phenyl or mono-, di-, tri-C1-C4-alkylphenyl, optically active compound.

A variant for bringing about enantiomerically or diastereomerically enriched, or enantiomerically or diastereomerically pure compounds, is provided by a method for preparing astaxanthin of the formula 1,

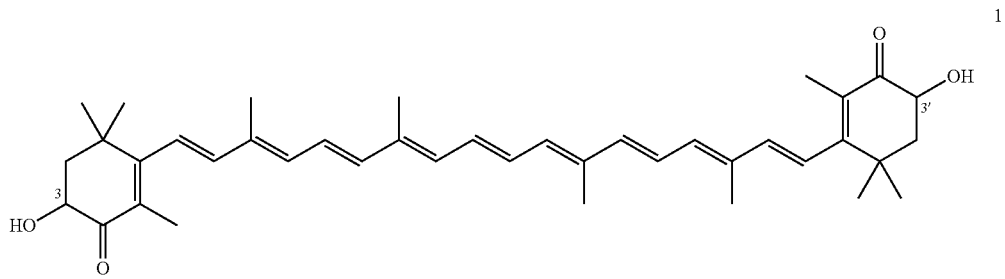 [SMILES: CC1=C(/C=C/C(C)=C/C=C/C(C)=C/C=C/C=C(C)/C=C/C=C(C)/C=C/C2=C(C)C(=O)C(O)CC2(C)C)C(C)(C)CC(O)C1=O]

in which the asymmetric center in position 3 and 3' has (S) or (R) configuration and the exocyclic double bonds have either E or E and/or Z configuration, in which astacin of the formula 2 according to the invention,

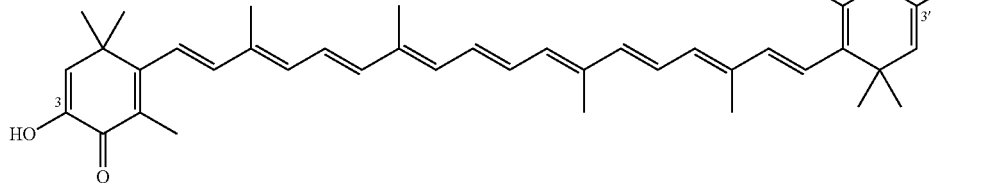

in which the exocyclic double bonds have either E or E and/or Z configuration, is reacted stereoselectively under basic conditions, preferably in a pH range of 8 to 12, with a reducing agent selected from the group consisting of formic acid, the salts of formic acid, isopropanol or butan-2-ol, in the presence of an optically active transition metal catalyst, wherein the optically active transition metal catalyst comprises ruthenium (Ru) as transition metal and at least one ligand selected from the group consisting of $H_2N$—CHPh-CHPh-OH, $H_2N$—CHMe-CHPh-OH, MeHN—CHMe-CHPh-OH, TsNH—CHPh-CHPh-$NH_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide, N-[(1R,2R)-1,2-diphenyl-2-(2-(4-methylbenzyloxy)ethylamino)ethyl]-4-methylbenzene sulfonamide, an optically active amino acid.

If an inventive transition metal catalyst is unable to maintain its activity in supported form, it has to be used in liquid phase.

Therefore, the method according to the invention is in many cases typically carried out in liquid phase, i.e. in at least one solvent or solvent mixture. The liquid phase preferably comprises at least one organic solvent, in which the liquid phase is typically composed of more than 50% by volume of organic solvents.

A further design variant of the invention therefore provides that the astacin 2 is reacted non-stereoselectively or stereoselectively with a reducing agent in a liquid medium, preferably in a liquid medium comprising more than 50% by volume of at least one organic solvent.

A liquid medium is understood to mean any monophasic or multiphasic liquid composition of a solvent or a solvent mixture. The liquid medium, therefore, is selected from the group of dichloromethane, ethylene glycol dimethyl ether, diethylene glycol dimethyl ether, tetrahydrofuran, ethylene carbonate, propylene carbonate, dimethyl formamide, dimethyl sulfoxide, ethyl acetate, n-propyl acetate, toluene, xylene, heptane, hexane, pentane, N-methyl-2-pyrrolidone, dioxane, 2-methyltetrahydrofuran, acetonitrile, methyl tert-butyl ether, diisopropyl ether, diethyl ether, di-n-butyl ether, water or a mixture of at least two of these solvents.

If the proportion of organic solvent is selected to be greater than 50% by volume, the reaction reactants and reaction products readily dissolve such that a rapid reaction is ensured.

In the reaction of the astacin 2 with the reducing agent in the presence of the transition metal catalyst, salts often occur, even in a reaction under basic conditions. These usually dissolve well in water and can then be readily removed. The liquid medium can, therefore, particularly comprise water as inorganic solvent.

An even further variant of the method according to the invention therefore specifies that the astacin 2 is reacted non-stereoselectively or stereoselectively with a reducing agent in a liquid medium, preferably in a liquid medium comprising more than 50% by volume of at least one organic solvent and comprising water as inorganic solvent.

Depending on the composition of the liquid medium composed of different solvents, the liquid medium may be a monophasic, biphasic or also multiphasic system.

Solubilities and therefore reaction rates differ from starting compound to starting compound. By way of various experiments, some solvents or mixtures thereof have been found to be particularly suitable. The solvents used are particularly mixtures of dichloromethane, ethylene glycol dimethyl ether, diethylene glycol dimethyl ether, and also THF and water.

Consequently, a development of the invention provides under protection that the organic solvent comprises at least one compound selected from the group consisting of dichloromethane, ethylene glycol dimethyl ether, diethylene glycol dimethyl ether, tetrahydrofuran, ethylene carbonate, propylene carbonate, dimethylformamide, dimethyl sulfoxide, ethyl acetate, n-propyl acetate, toluene, xylene, heptane, hexane, pentane, N-methyl-2-pyrrolidone, dioxane, 2-methyltetrahydrofuran, methyl tert-butyl ether, diisopropyl ether, diethyl ether, di-n-butyl ether, acetonitrile and preferably from the group consisting of dichloromethane, ethylene glycol dimethyl ether, diethylene glycol dimethyl ether, tetrahydrofuran, acetonitrile, ethylene carbonate and propylene carbonate.

By way of various experiments, the following embodiment has proven to be particularly suitable with regard to yield and purity of the astaxanthin 1 obtained. Said embodiment specifies that the astacin 2 is reacted non-stereoselectively or stereoselectively with a reducing agent in a liquid medium, preferably in a liquid medium comprising more than 50% by volume of at least one organic solvent selected from the group consisting of dichloromethane, ethylene glycol dimethyl ether, diethylene glycol dimethyl ether, tetrahydrofuran, acetonitrile, propylene carbonate, ethylene carbonate and comprising water as inorganic solvent.

Another continuation of the invention results in high yields after a brief reaction time. This development comprises a method for preparing astaxanthin of the formula 1

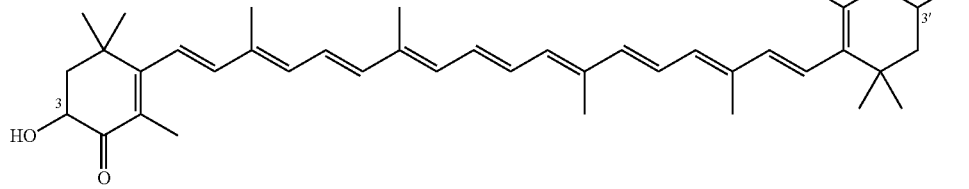

in which the asymmetric center in position 3 and 3' is racemic or has (S) or (R) configuration and the exocyclic double bonds have either E or E and/or Z configuration, in which astacin of the formula 2 according to the invention,

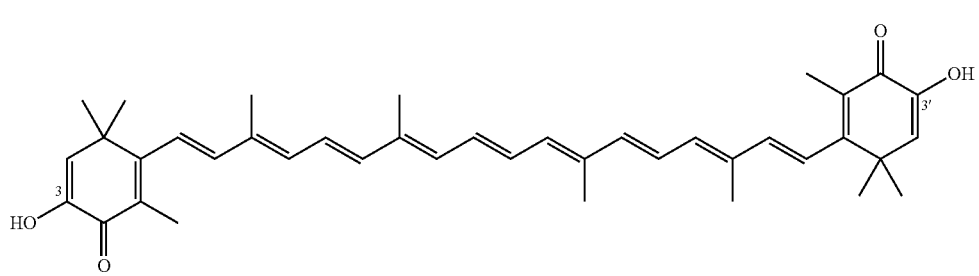

in which the exocyclic double bonds have either E or E and/or Z configuration, is reacted non-stereoselectively or stereoselectively in a liquid medium under basic conditions, preferably in a pH range of 8 to 12, with a reducing agent selected from the group consisting of formic acid and/or the salts of formic acid, isopropanol, butan-2-ol, in the presence of a transition metal catalyst, wherein the transition metal catalyst comprises ruthenium (Ru) as transition metal and at least one ligand selected from the group consisting of H$_2$N—CH$_2$—CH$_2$—OH, MeHN—CH$_2$—CH$_2$—OH, H$_2$N—CH$_2$—CH$_2$—NH$_2$, TsNH—CH$_2$—CH$_2$—NH$_2$, TsNH—CH$_2$—CH$_2$—NH—(CH$_2$)$_n$—O$_m$—(CH$_2$)$_o$-aryl where n=1-4, m=0 or 1 and o=1-4 and aryl=phenyl or mono-, di-, tri-C1-C4-alkylphenyl, optically active compound, and wherein the liquid medium comprises more than 50% by volume of at least one organic solvent selected from the group consisting of dichloromethane, ethylene glycol dimethyl ether, diethylene glycol dimethyl ether, tetrahydrofuran, acetonitrile, propylene carbonate, ethylene carbonate.

This applies also to the variant for generating highly enantiomerically/diastereomerically enriched compounds or enantiomerically/diastereomerically pure compounds. This development describes a method for preparing astaxanthin of the formula 1,

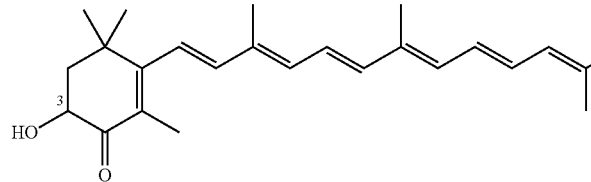

in which the asymmetric center in position 3 and 3' has (S) or (R) configuration and the exocyclic double bonds have either E or E and/or Z configuration, in which astacin of the formula 2 according to the invention,

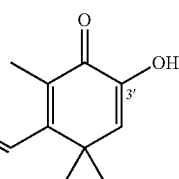

in which the exocyclic double bonds have either E or E and/or Z configuration, is reacted stereoselectively in a liquid medium under basic conditions, preferably in a pH range of 8 to 12, with a reducing agent selected from the group consisting of formic acid, the salts of formic acid, isopropanol or butan-2-ol, in the presence of an optically active transition metal catalyst, wherein the optically active transition metal catalyst comprises ruthenium (Ru) as transition metal and at least one ligand selected from the group consisting of H$_2$N—CHPh-CHPh-OH, H$_2$N—CHMe-CHPh-OH, MeHN—CHMe-CHPh-OH, TsNH—CHPh-CHPh-NH$_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide, N-[(1R,2R)-1,2-diphenyl-2-(2-(4-methylbenzyloxy)ethylamino)ethyl]-4-methylbenzene sulfonamide, an optically active amino acid and wherein the liquid medium comprises more than 50% by volume of at least one organic solvent selected from the group consisting of dichloromethane, ethylene glycol dimethyl ether, diethylene glycol dimethyl ether, tetrahydrofuran, acetonitrile, propylene carbonate, ethylene carbonate.

A further advantage of the method according to the invention is that said method affords high yields of astaxanthin 1 also at low temperatures in a reasonable time. Consequently, the subject matter of a further modification of the invention is that the astacin 2 is reacted non-stereoselectively or stereoselectively with a reducing agent at a temperature of 10° C. to 85° C.; preferably 20° C. to 60° C.

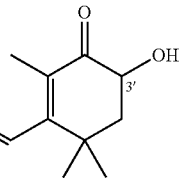

The method according to the invention may also of course be carried out under pressure. The preferred pressure range is between 0 and 10 bar. The particularly preferred temperature range also under pressure is from 20 to 60° C.

The reaction may be carried out discontinuously in batch or semi-batch mode or continuously in the customary apparatus known to the person skilled in the art. Examples include stirred tank, stirred tank cascade and tubular reactors.

The workup is also carried out by customary methods. Preference is given to extraction and crystallization.

Astacin 2 may be used for the synthesis of astaxanthin 1, where both racemic mixtures and the meso form and all enantiomerically pure representatives of astaxanthin fall under the term astaxanthin.

Therefore, the invention also relates to the use of astacin 2 as intermediate for preparing (3R/S, 3R/S)-astaxanthin 1a, wherein the exocyclic double bonds in 1a have either E or E and/or Z configuration (3R/S, 3'R/S)-Astaxanthin 1a

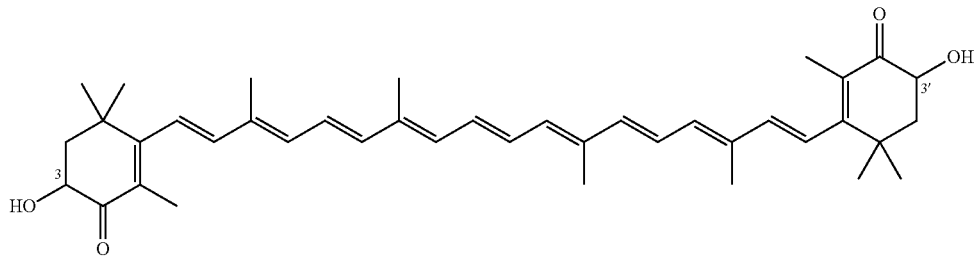

and/or (3S,3'S)-astaxanthin 1b, wherein the exocyclic double bonds in 1b have either E or E and/or Z configuration (3S, 3'S)-Astaxanthin 1b

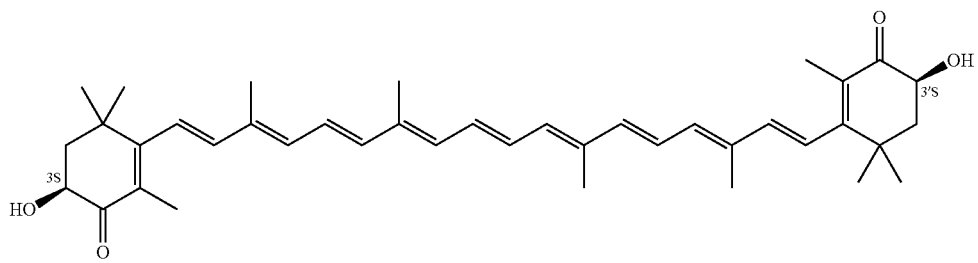

and/or (3R,3'R)-astaxanthin 1c, wherein the exocyclic double bonds in 1c have either E or E and/or Z configuration (3R, 3'R)-Astaxanthin 1c

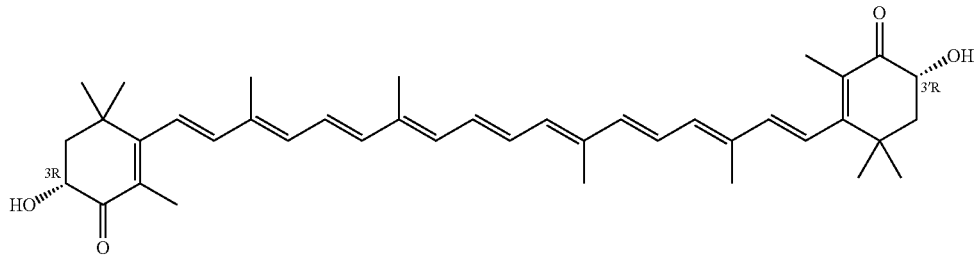

Further characteristics, details and advantages of the invention are apparent from the wording of the claims and also from the working examples described below.

EXAMPLES

Example 1

Synthesis of (3S,3'S)-astaxanthin (3S,3'S)-1 from astacin 2

0.5 g (0.8 mmol) of astacin 2 are charged in 20 ml of dichloromethane at 22° C., 1.01 g (10.02 mmol) of triethylamine and 5.1 mg (0.01 mmol) of chloro{[(1S,2S)-(+)-2-amino-1,2-diphenylethyl](4-toluenesulfonyl)amido}(p-cymene)ruthenium(II) are added, 0.37 g (8.01 mmol) of formic acid are added dropwise and the mixture is heated to 40° C. for 7.5 h. After cooling to 20° C., 10 ml of water are added, the phases separated and the organic phase washed with 10 ml of water. The organic phase is then concentrated on a rotary evaporator. The residue is suspended in 2.7 ml of methanol and heated to 106° C. for 4 h and then concentrated again. 0.523 g (71.38% strength, yield: 78%) of (3S,3'S)-astaxanthin 1b are obtained with a diastereomeric excess of 98% and an enantiomeric excess of >99%.

Example 2

Synthesis of (3R/S,3'R/S)-astaxanthin (3R/S,3'R/S)-1 from astacin 2

1.0 g (1.67 mmol) of astacin 2 are charged in 20 ml of dichloromethane at 22° C., 2.11 g (20.85 mmol) of triethylamine and 8.09 mg (0.02 mmol) of chloro{[2-aminoethyl](4-toluenesulfonyl)amido}(p-cymene)ruthenium(II) are added, 0.77 g (16.68 mmol) of formic acid are added dropwise and the mixture is heated to 40° C. for 4.5 h. After cooling to 20° C., 15 ml of water are added, the phases separated and the organic phase washed with 15 ml of water. The organic phase is then concentrated on a rotary evaporator. The residue is suspended in 6 ml of methanol heated to 106° C. for 4 h and then concentrated again. 0.72 g (88.1% strength, yield: 63.7%) of (3R/S,3'R/S)-astaxanthin 1a are obtained.

Example 3

2.0 g (3.31 mmol) of astacin 2 are charged in 40 ml of dichloromethane at 22° C., 4.19 g (41.4 mmol) of triethylamine and 21.1 mg (0.03 mmol) of chloro{[(1R,2R)-(+)-2-amino-1,2-diphenylethyl](4-toluenesulfonyl)amido}(p-cymene)ruthenium(II) are added and 1.51 g (33.1 mmol) of formic acid are added dropwise at 22-35° C. The reaction mixture is heated to 40° C. for 7 h. 15 ml of water is added to the mixture and the phases are separated. The organic phase is washed with 40 ml of 10% strength acetic acid and 40 ml of saturated sodium hydrogen carbonate solution and then concentrated on a rotary evaporator. The residue is suspended in 12 ml of methanol heated to 106° C. for 4 h and, after cooling to 0° C., filtered off, washed with 3 ml of methanol and dried in a vacuum drying cabinet at 20° C. 1.21 g (93.3% strength, yield: 57%) of (3R,3R)-astaxanthin 1c are obtained with a diastereomeric excess of 97% and an enantiomeric excess of >99%.

It is evident that the invention relates to a method for the non-stereoselective and also for the stereoselective synthesis of astaxanthin from astacin. For this purpose, a reducing agent is used selected from the group of hydrogen, a secondary alcohol, formic acid and also the salts of formic acid or from a mixture of at least two representatives of the compound classes stated above. The invention further relates to the use of astacin as starting compound for the synthesis of astaxanthin.

The invention claimed is:

1. A method for preparing astaxanthin of the formula (1)

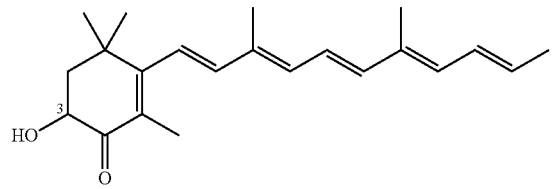

(1)

in which the asymmetric center in position 3 and 3' is racemic or each has (S) or (R) configuration and the exocyclic double bonds have either E or E and/or Z configuration, wherein astacin of the formula (2),

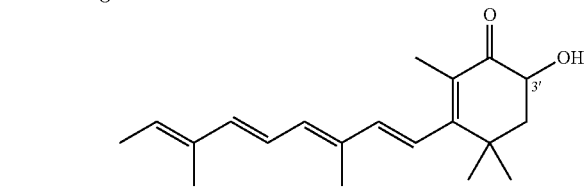

(2)

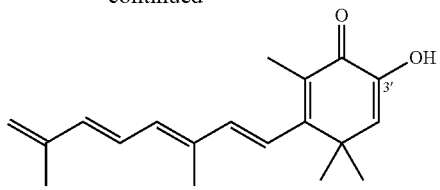

in which the exocyclic double bonds have either E or E and/or Z configuration, is reacted non-stereoselectively or stereoselectively with a reducing agent.

2. The method according to claim 1, wherein the reducing agent is at least one compound selected from the group consisting of hydrogen gas; a secondary alcohol, formic acid or the salts of formic acid.

3. The method according to claim 1, wherein the reducing agent is at least one compound selected from the group consisting of hydrogen gas; isopropanol; butan-2-ol; formic acid, an alkali metal, alkaline earth metal or ammonium formate or a mono-, di-, tri- or tetra(C1-C4)-alkylammonium formate.

4. The method according to claim 1, wherein the astacin (2) is reacted non-stereoselectively or stereoselectively with the reducing agent in the presence of a transition metal catalyst.

5. The method according to claim 1, wherein the astacin (2) is reacted non-stereoselectively or stereoselectively with the reducing agent in the presence of an achiral or optically active transition metal catalyst.

6. The method according to claim 3, wherein the transition metal catalyst comprises a transition metal selected from the group consisting of Ti, Zr, Hf, V, Nb, Ta, Cr, Mo, W, Mn, Re, Fe, Ru, Os, Co, Rh, Ir, Ni, Pd, Pt, Cu, Ag and Au.

7. The method according to claim 3, wherein the transition metal catalyst comprises a transition metal selected from the group consisting of Ru, Ir, Ni and Pd.

8. The method according to claim 3, wherein the transition metal catalyst comprises at least one ligand selected from amines and/or phosphanes.

9. The method according to claim 8, wherein the ligand is a phosphane of the general formula (3),

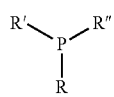

3 where R, R' and R'' are each independently selected from the group consisting of at least one of the residues C1-C4-alkyl, phenyl, mono- up to tri-C1-C4-alkyl-substituted aryl; and a triarylphosphane.

10. The method according to claim 8, wherein the ligand is a phosphane of the general formula (3),

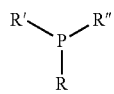

3 where R, R' and R'' are each independently selected from the group consisting of a triphenylphosphane.

11. The method according to claim 3, wherein the transition metal catalyst comprises at least one ligand selected from the group consisting of $H_2N$—$CH_2$—$CH_2OH$, MeHN—$CH_2$—$CH_2$—OH, $H_2N$—$CH_2$—$CH_2$—$NH_2$, TsNH—$CH_2$—$CH_2$—$NH_2$, TsNH—$CH_2$—$CH_2$—NH—$(CH_2)_n$—$O_m$—$(CH_2)_o$-aryl where n=1-4, m=0 or 1 and o=1-4 and aryl=phenyl or mono-, di-, tri-C1-C4-alkylphenyl, optically active compound.

12. The method according to claim 3, wherein the transition metal catalyst comprises at least one ligand selected from the group consisting of an optically active amine.

13. The method according to claim 3, wherein the transition metal catalyst comprises at least one ligand selected from the group consisting of $H_2N$—CHPh-CHPh-OH, $H_2N$—CHMe-CHPh-OH, MeHN—CHMe-CHPh-OH, TsNH—CHPh-CHPh-$NH_2$, (1S,2S)—N-p-toluenesulfonyl-1,2-diphenyl ethylenediamine, (1R,2R)—N-p-toluenesulfonyl-1,2-diphenyl ethylenediamine, N-[(1S,2S)-1,2-diphenyl-2-(2-(4-methylbenzyloxy)ethylamino)ethyl]-4-methylbenzene sulfonamide and N-[(1R,2R)-1,2-diphenyl-2-(2-(4-methylbenzyloxy)ethylamino)ethyl]-4-methylbenzene sulfonamide.

14. The method according to claim 5, wherein the ligand is deprotonated.

15. The method according to claim 4, wherein the transition metal is applied to a solid support comprising at least one substance selected from the group consisting of carbon, aluminum oxide and silicon dioxide.

16. The method according to claim 1, wherein the astacin (2) is reacted non-stereoselectively or stereoselectively with a reducing agent under basic conditions.

17. The method according to claim 1, wherein the astacin (2) is reacted non-stereoselectively or stereoselectively with a reducing agent in a liquid medium.

18. The method according to claim 17, wherein said liquid medium comprising more than 50% by volume of at least one organic solvent and said organic solvent comprises at least one compound selected from the group consisting of dichloromethane, ethylene glycol dimethyl ether, diethylene glycol dimethyl ether, tetrahydrofuran, acetonitrile, ethylene carbonate and propylene carbonate.

19. The method according to claim 1, wherein the astacin (2) is reacted non-stereoselectively or stereoselectively with a reducing agent at a temperature of 10° C. to 85° C.

\* \* \* \* \*